US012128166B2

(12) United States Patent
Crook et al.

(10) Patent No.: US 12,128,166 B2
(45) Date of Patent: Oct. 29, 2024

(54) SYSTEMS AND METHODS FOR USING NITRIC OXIDE IN DIALYSIS

(71) Applicant: Fresenius Medical Care Holdings, Inc., Waltham, MA (US)

(72) Inventors: Nathan Crook, Ogden, UT (US); Ryan Andersen, Ogden, UT (US); Kylie Colvin, Ogden, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 18/528,431

(22) Filed: Dec. 4, 2023

(65) Prior Publication Data

US 2024/0197974 A1 Jun. 20, 2024

Related U.S. Application Data

(60) Provisional application No. 63/433,357, filed on Dec. 16, 2022.

(51) Int. Cl.
*A61M 1/34* (2006.01)
*B01D 61/24* (2006.01)

(52) U.S. Cl.
CPC ........ *A61M 1/3462* (2013.01); *A61M 1/3413* (2013.01); *A61M 1/3479* (2014.02); *B01D 61/243* (2013.01); *A61M 2202/0275* (2013.01)

(58) Field of Classification Search
CPC .............. A61M 1/3462; A61M 1/3413; A61M 1/3479; A61M 2202/0275; B01D 61/243
See application file for complete search history.

(56) References Cited

U.S. PATENT DOCUMENTS

| 5,725,492 A | 3/1998 | Igo et al. |
| 5,957,880 A | 9/1999 | Igo et al. |
| 7,485,324 B2 | 2/2009 | Miller et al. |
| 8,216,478 B2 | 7/2012 | Noack et al. |
| 9,629,358 B2 | 4/2017 | Potenziano et al. |
| 10,172,994 B2 | 1/2019 | Tschulena et al. |

(Continued)

FOREIGN PATENT DOCUMENTS

| CN | 113797404 A | 12/2021 |
| EP | 2805730 A1 | 11/2014 |

(Continued)

OTHER PUBLICATIONS

International Patent Application No. PCT/US2023/082302, International Search Report (Apr. 11, 2024).
Ayati, Roya "Methemoglobin Formation via Nitric Oxide and Comparison of Methemoglobin, Deoxyhemoglobin, and Ferrous Nitrosyl Hemoglobin as Potential MRI Contrast Agents," Thesis, Brigham Young University (Dec. 13, 2022).

(Continued)

*Primary Examiner* — Pranav N Patel
(74) *Attorney, Agent, or Firm* — Leydig, Voit & Mayer, Ltd.

(57) ABSTRACT

A hemodiafiltration (HDF) system is provided for performing HDF treatment. The HDF system includes a mixing system for mixing nitric oxide (NO) with other chemicals to produce a dialysis fluid. The HDF system further includes an extracorporeal blood circuit that includes a filter for separating the dialysis fluid into a dialysate and NO spiked substitution fluid. The extracorporeal blood circuit also includes a dialyzer that receives the dialysate and a blood line connected to the dialyzer. The blood line includes admission points connected to the filter. The admission points are used to administer the NO spiked substitution fluid to the patient during the HDF treatment.

15 Claims, 6 Drawing Sheets

(56) References Cited

U.S. PATENT DOCUMENTS

| | | |
|---|---|---|
| 10,328,099 B2 | 6/2019 | Sherman |
| 10,821,216 B1 | 11/2020 | Collins et al. |
| 10,898,512 B2 | 1/2021 | Sherman |
| 2006/0068031 A1 | 3/2006 | Miller et al. |
| 2007/0154570 A1 | 7/2007 | Miller et al. |
| 2008/0233212 A9 | 9/2008 | Miller et al. |
| 2014/0272920 A1 | 9/2014 | Potenziano et al. |
| 2017/0165293 A1 | 6/2017 | Dasse et al. |
| 2018/0256637 A1 | 9/2018 | Sherman |
| 2019/0039910 A1 | 2/2019 | Handa et al. |
| 2019/0255098 A1 | 8/2019 | Sherman |
| 2020/0253926 A1 | 8/2020 | Cowen et al. |
| 2021/0077524 A1 | 3/2021 | Sherman |
| 2021/0154373 A1 | 5/2021 | Park et al. |
| 2021/0268156 A1 | 9/2021 | Handa et al. |
| 2022/0331500 A1 | 10/2022 | Kokubo et al. |

FOREIGN PATENT DOCUMENTS

| | | |
|---|---|---|
| WO | WO 01/65935 A1 | 9/2001 |
| WO | WO 01/78805 A1 | 10/2001 |
| WO | WO 02/056864 A2 | 7/2002 |
| WO | WO 2005/004884 A2 | 1/2005 |
| WO | WO 2005/007173 A1 | 1/2005 |
| WO | WO 2010/056726 A1 | 5/2010 |
| WO | WO 2010/065917 A1 | 6/2010 |
| WO | WO 2011/003172 A1 | 1/2011 |
| WO | WO 2013/070592 A1 | 5/2013 |
| WO | WO 2013/181322 A1 | 12/2013 |
| WO | WO 2015/084698 A2 | 6/2015 |
| WO | WO 2018/165098 A1 | 9/2018 |
| WO | WO 2021/015235 A1 | 1/2021 |
| WO | WO 2022/017763 A1 | 1/2022 |

OTHER PUBLICATIONS

Bohlen et al., "Transfer of Nitric Oxide by Blood From Upstream to Downstream Resistance Vessels Causes Microvascular Dilation," *Am. J. Physiol. Heart Circ. Physiol.*, 297, H1337-H1346 (2009).

Douma et al., "Icodextrin with Nitroprusside Increases Ultrafiltration and Peritoneal Transport During Long CAPD Dwells," *Kidney International*, 53 (4), 1014-1021 (1998).

Imamović et al., "Principles of Haemodiafiltration: Rationale for Improved Patients' Survival," *Advances in Hemodiafiltration*, Chapter 2 (2016).

Kokubo et al., "Suppression of Blood Coagulation on the Surface of a Dialysis Membrane Using a Nitric Oxide Containing Dialysate," *Nephrology Dialysis Transplantation*, 34 (Supp. 1) (2019).

Lei et al., "Nitric Oxide Decreases Acute Kidney Injury and Stage 3 Chronic Kidney Disease After Cardiac Surgery," *Am. J. Respiratory and Critical Care Med.*, 198 (10), 1279-1287 (Nov. 15, 2018).

Rocchitta et al.," Signalling Pathways in the Nitric-Oxide Donor-Induced Dopamine Release in the Striatum of Freely Moving Rats: Evidence That Exogenous Nitric Oxide Promotes $Ca^2+$ entry Through Store-Operated Channels" *Brain Research*, 1023, 243-252 (2004).

Ukaigwe et al. "Recurrent Non-Occlusive Mesenteric Ischemia During Dialysis" *J. General Internal Medicine*, S447 (2015).

Urabe et al. "Suppression of Platelet Reactivity During Dialysis by Addition of a Nitric Oxide Donor to the Dialysis Fluid," *Renal Replacement Therapy* (2020).

Wisniak, Jamie "Thomas Graham. II.: Contributions to diffusion of gases and liquids, colloids, dialysis, and osmosis," *Educación Química* (Nov. 2013).

Zhou et al. "Water-Soluble Poly(ethylenimine)-Based Nitric Oxide Donors: Preparation, Characterization, and Potential Application in Hemodialysis" *Biomacromolecules*, 7, 2565-2574 (2006).

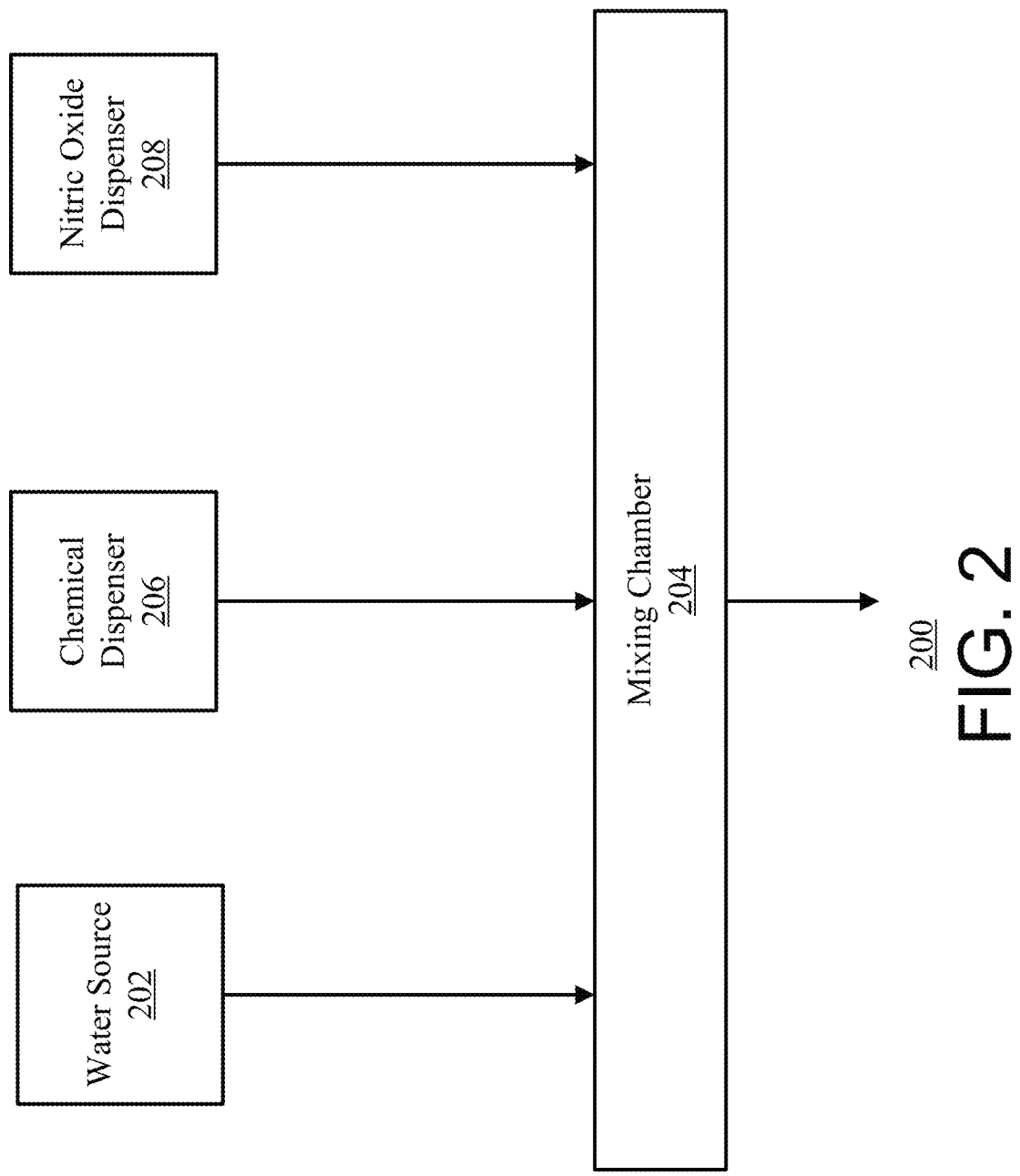

SYSTEMS AND METHODS FOR USING NITRIC OXIDE IN DIALYSIS

CROSS-REFERENCE TO RELATED APPLICATIONS

This patent application claims the benefit of U.S. Provisional Patent Application No. 63/433,357, filed Dec. 16, 2022, which is incorporated by reference herein in its entirety.

BACKGROUND

Various methods of extracorporeal blood treatment are used to remove toxic substances and excess water from chronic kidney disease patients. Many of these toxins are eliminated in urine by healthy patients. In hemodialysis, the patient's blood is cleaned outside the body by passing the patient's blood through a dialyzer. The dialyzer comprises a blood chamber and a dialysis fluid chamber which are separated by a semipermeable membrane. During the treatment, the patient's blood flows through the blood chamber. In order to clean the blood effectively from substances usually eliminated with urine, fresh dialysis fluid flows continuously through the dialysis fluid chamber, which removes water and toxins by the processes of diffusion and convection.

Whereas the transport of lower-molecular weight substances through the membrane of the dialyzer is essentially determined by the concentration differences (diffusion) between the dialysis fluid and the blood in the case of hemodialysis (HD), substances dissolved in the plasma water component of the blood, in particular higher-molecular weight substances, are effectively removed by a high fluid flow (convection) through the membrane of the dialyzer in the case of hemofiltration (HF). In HF, the dialyzer functions as a filter. Hemodiafiltration (HDF) is a combination of the two processes.

In HDF, part of the plasma water drawn through the membrane of the dialyzer must be replaced by a sterile substitution fluid, which is generally fed to the extracorporeal blood circuit either upstream (pre-dilution) or downstream (post-dilution) of the dialyzer. Mechanisms for HDF are known, wherein the dialysis fluid is prepared online from sterile water and dialysis fluid concentrate and this substitution fluid is prepared online from the dialysis fluid.

However, when compared to HD, HDF associated convection causes more endothelial stress when used to remove higher-molecular-weighted substances. HDF is also more costly, requires more training of clinical staff, and is associated with greater loss of desirable blood proteins such as albumin. Accordingly, HDF is sometimes limited to acute care (short-term) settings. Additionally, certain patients (e.g., those having high blood pressure or with other co-morbidities) struggle with HDF as it produces more strain and stress on the patient's body when compared to HD. Accordingly, there remains a technical need to reduce endothelial and/or other types of stress to a patient's body during HDF treatment. Methods also need to be developed to expand the availability of the HDF treatment to patients having certain co-morbidities such as high blood pressure.

SUMMARY

This summary is provided to introduce certain exemplary embodiments that are further described below. This summary is not intended to be an identification of key features or essential features of the present disclosure.

In some instances, a hemodiafiltration (HDF) system for performing HDF treatment is provided. The HDF system comprises a mixing system, an extracorporeal blood circuit, and a controller. The mixing system comprises a nitric oxide dispenser configured to provide nitric oxide (NO) to a mixing chamber; a chemical dispenser configured to provide chemicals to the mixing chamber; and a mixing chamber configured to mix the NO and the chemicals to produce a dialysis fluid. The extracorporeal blood circuit comprises: a filter configured to separate the dialysis fluid into a dialysate and NO spiked substitution fluid; a dialyzer configured to receive the dialysate from the filter; and a blood line connected to the dialyzer and comprising one or more admission points, wherein one or more admission points are connected to the filter to deliver NO spiked substitution fluid administered during the HDF treatment using the one or more admission points. The controller is configured to provide instructions to the mixing system to produce the dialysis fluid comprising the NO; and provide instructions to the extracorporeal blood circuit to perform the HDF treatment using the dialysate and NO spiked substitution fluid.

In some examples, the blood line comprises an arterial blood line and a venous blood line, wherein the arterial blood line feeds blood from the patient to a blood chamber of the dialyzer, wherein the venous blood line provides the blood of the patient from the blood chamber back to the patient, and wherein the one or more admission points is an arterial admission point that is on the arterial blood line and configured to provide the NO spiked substitution fluid prior to the blood chamber for pre-dilution HDF treatment.

In some variations, the blood line comprises an arterial blood line and a venous blood line, wherein the arterial blood line feeds blood from the patient to a blood chamber of the dialyzer, wherein the venous blood line provides the blood of the patient from the blood chamber back to the patient, and wherein the one or more admission points is a venous admission point that is on the venous blood line and configured to provide the NO spiked substitution fluid after the blood chamber for post-dilution HDF treatment.

In some instances, the filter comprises a membrane, a first chamber, and a second chamber, and wherein the filter is configured to separate the dialysis fluid by having a first portion of the dialysis fluid not pass through the membrane and remain in the first chamber and a second portion of the dialysis fluid pass through the membrane to enter the second chamber, wherein the first portion of the dialysis fluid is the dialysate and the second portion of the dialysis fluid is the NO spiked substitution fluid.

In some examples, the extracorporeal blood circuit further comprises: a dialysate line that connects the first chamber of the filter to the dialyzer; and a substitution fluid line that connects the second chamber of the filter to the one or more admission points.

In some variations, the nitric oxide dispenser comprises a nitric oxide source, and wherein the nitric oxide source provides nitric oxide in a liquid form.

In some instances, the nitric oxide dispenser comprises a nitric oxide source, and wherein the nitric oxide source provides nitric oxide in a gaseous form.

In some examples, providing the instructions to the mixing system to produce the dialysis fluid comprises: providing instructions to the nitric oxide dispenser to dispense a set amount of NO to the mixing chamber.

In some variations, the extracorporeal blood circuit further comprises: a pump configured to pump the NO spiked substitution fluid into the one or more admission points, and wherein providing the instructions to the extracorporeal blood circuit to perform the HDF treatment comprises controlling a rate that the pump supplies the NO spiked substitution fluid into the one or more admission points.

In some examples, a hemodiafiltration (HDF) system for performing HDF treatment is provided. The HDF system comprises a controller configured to: provide instructions to produce dialysis fluid comprising nitric oxide (NO); and provide instructions to perform the HDF treatment using the dialysis fluid comprising the NO. The HDF system further comprises an extracorporeal blood circuit comprising: a filter configured to separate the dialysis fluid into a dialysate and NO spiked substitution fluid; a dialyzer configured to receive the dialysate from the filter; and a blood line connected to the dialyzer and comprising one or more admission points for administering the NO spiked substitution fluid during the HDF treatment.

In some instances, the blood line comprises an arterial blood line and a venous blood line, and wherein the one or more admission points is an arterial admission point that is on the arterial blood line and configured to administer the NO spiked substitution fluid prior to the dialyzer for pre-dilution HDF treatment.

In some variations, the blood line comprises an arterial blood line and a venous blood line, and wherein the one or more admission points is a venous admission point that is on the venous blood line and configured to administer the NO spiked substitution fluid after the dialyzer for post-dilution HDF treatment.

In some examples, the filter comprises a membrane, a first chamber, and a second chamber, and wherein the filter is configured to separate the dialysis fluid by having a first portion of the dialysis fluid not pass through the membrane and remain in the first chamber and a second portion of the dialysis fluid pass through the membrane to enter the second chamber, wherein the first portion of the dialysis fluid is the dialysate and the second portion of the dialysis fluid is the NO spiked substitution fluid.

In some instances, the extracorporeal blood circuit further comprises: a dialysate line that connects the first chamber of the filter to the dialyzer; and a substitution fluid line that connects the second chamber of the filter to the one or more admission points.

In some variations, providing the instructions to produce the dialysis fluid comprising NO comprises: providing instructions to a nitric oxide dispenser to dispense a set amount of NO to a mixing chamber.

In some variations, a method for performing hemodiafiltration (HDF) treatment is provided. The method comprises: producing dialysis fluid comprising nitric oxide (NO) for performing the HDF treatment for a patient; and performing the HDF treatment for the patient using an HDF system, wherein the HDF system comprises extracorporeal circuits, wherein the extracorporeal circuits comprises a filter for separating the dialysis fluid into a dialysate and NO spiked substitution fluid, a dialyzer for receiving the dialysate from the filter, and a blood line connected to the dialyzer and comprising one or more admission points for administering the NO spiked substitution fluid during the HDF treatment.

In some instances, the blood line comprises an arterial blood line and a venous blood line, wherein the arterial blood line feeds blood from the patient to a blood chamber of the dialyzer, wherein the venous blood line provides the blood of the patient from the blood chamber back to the patient, wherein the one or more admission points is an arterial admission point that is on the arterial blood line, and wherein performing the HDF treatment for the patient comprises: performing pre-dilution HDF treatment based on using the arterial admission point to provide the NO spiked substitution fluid prior to the blood chamber.

In some examples, the blood line comprises an arterial blood line and a venous blood line, wherein the arterial blood line feeds blood from the patient to a blood chamber of the dialyzer, wherein the venous blood line provides the blood of the patient from the blood chamber back to the patient, wherein the one or more admission points is a venous admission point that is on the venous blood line, and wherein performing the HDF treatment for the patient comprises: performing post-dilution HDF treatment based on using the venous admission point to provide the NO spiked substitution fluid after the blood chamber.

In some variations, the filter comprises a membrane, a first chamber, and a second chamber, and wherein the filter is configured to separate the dialysis fluid by having a first portion of the dialysis fluid not pass through the membrane and remain in the first chamber and a second portion of the dialysis fluid pass through the membrane to enter the second chamber, wherein the first portion of the dialysis fluid is the dialysate and the second portion of the dialysis fluid is the NO spiked substitution fluid.

In some instances, producing the dialysis fluid comprising the NO for performing the HDF treatment for the patient comprises: providing instructions to a nitric oxide dispenser to dispense a set amount of NO to a mixing chamber.

Further features and aspects are described in additional detail below with reference to the FIGs.

BRIEF DESCRIPTION OF THE DRAWINGS

FIG. 2 shows a block diagram illustrating an exemplary mixing system according to one or more examples of the disclosure;

DETAILED DESCRIPTION

Figure 1:
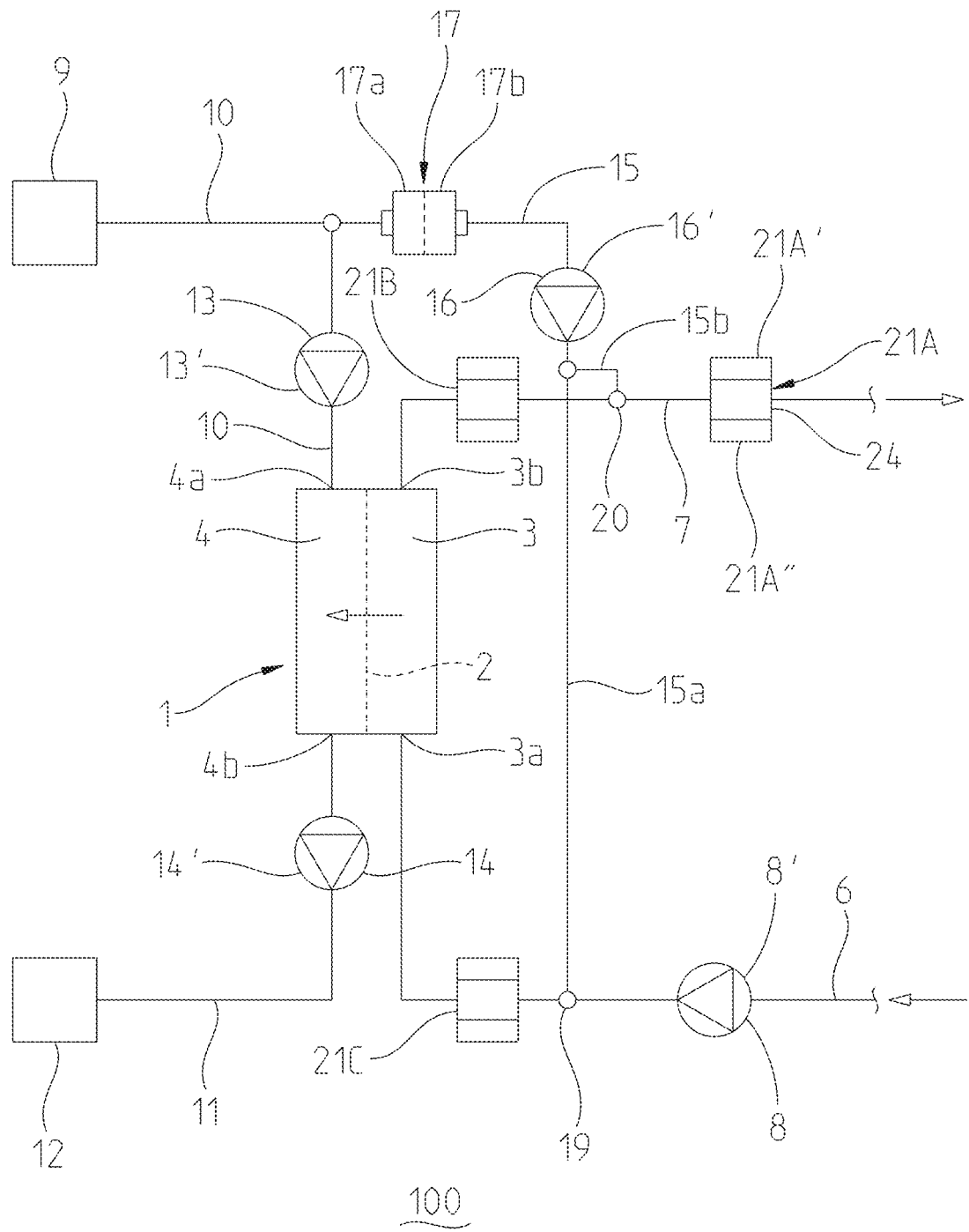
FIG. 1 shows an exemplary extracorporeal blood treatment apparatus for a hemodiafiltration system according to one or more examples of the disclosure.

Exemplary embodiments of the present application provide a hemodiafiltration (HDF) system using nitric oxide (NO). For instance, as mentioned above, compared to hemodialysis (HD) systems, HDF systems may cause more stress (e.g., endothelial stress) to the patient's body and also preclude certain patients (e.g., patients with high blood pressure) from using the HDF treatment. Furthermore, HDF systems cause greater fluid loss from the blood, and thus, may use substitution fluid (pre-dilution or post-dilution) prior to returning it to the patient. Accordingly, embodiments of the present application use nitric oxide (NO) to freely enter the bloodstream during HDF treatment. By introducing NO into the extracorporeal blood circuit, this may reduce endothelial stress on the patient associated with the HDF treatment and may further reduce the blood pressure of the patient. Furthermore, NO may further reduce inflammation during and after the HDF treatment as well as reduce platelet aggregation in the dialyzer. In some instances, an NO source (e.g., an NO donor) may be used that is and/or includes S-nitrosoglutathione and S-nitrosocysteine. S-nitrosoglutathione and S-nitrosocysteine may both be used due to their dissociation into nitric oxide and glutathione or cysteine, all of which are naturally found in the human body. In other instances, the NO source may be a NO gas that is dissolved in a liquid to be used for HDF treatment.

In some instances, embodiments of the present application include a system that is configured to dissolve gaseous NO into the water used for the substitution fluid, and infuse/mix the NO-dosed substitution fluid into blood through an extracorporeal blood circuit. In other instances, embodiments of the present application include a system that is configured to directly infuse gaseous NO into blood through the extracorporeal circulation (ECC) during the HDF treatment. Additionally, and/or alternatively, the system may administer the NO either pre-dilution and/or post-dilution. By using pre-dilution, the NO is exposed to the membrane (e.g., a semi-permeable membrane of the dialyzer), which provides reduced platelet aggregation at the membrane. This will be explained in further detail below.

In some examples, embodiments of the present application utilize administering an NO dose in a controlled manner over time, which may avoid significant side effects, including a sudden drop in the patient's blood pressure caused by administration of a bolus of NO. For example, because HDF systems use convection and diffusion, the dose of NO can be controlled much better in HDF than in HD systems. For instance, the process of diffusion alone makes it difficult for HD systems to control the amount of NO that is introduced to the patient through the dialysate. In contrast, HDF systems are capable of accurately controlling the dose of NO provided to the patient over a period of time by directly controlling the quantity of NO that enters the patient through spiked substitution fluid. The effects of NO are controlled by simultaneously measuring methemoglobin in the patient with CO oximetry to ensure a correct dosage.

In some variations, embodiments of the present application may distinguish NO added to the blood stream during HDF treatment from nitrates/nitrites/nitric oxides already present in the blood stream. In some instances, embodiments of the present application enable the system to perform accurate and precise measurements of nitric oxide administered during HDF treatment, use the NO donors to reduce platelet aggregation, and measure the performance of the NO donor in a continuous blood circuit (dialyzer and pump included), and the impact of that addition over time. In some examples, the NO donor is added to the blood directly. For instance, the system may administer NO dosed substitution fluid during HDF treatment either pre-dilution or post-dilution. Post-dilution infusion of NO may provide greater benefits to the patient's endothelial tissue (e.g., by reducing the endothelial stress). Pre-dilution infusion of NO may provide direct administration of the NO to the membrane. In other examples, the NO donor is added to the dialysate and is allowed to pass into the blood stream via convective transfer.

FIG. 1 shows an exemplary extracorporeal blood treatment apparatus for a hemodiafiltration system according to one or more examples of the disclosure. For example, FIG. 1 shows, in a schematic representation, an embodiment of a portion 100 of the HDF system that uses NO. FIG. 1 is merely exemplary and the HDF system can include additional and/or alternative components for performing HDF treatments using NO. Furthermore, certain components shown in FIG. 1 might not be within all HDF systems described herein.

The portion 100 of the HDF system includes a dialyzer (1), which is divided by a semi-permeable membrane (2) into a first chamber (3), through which blood flows and which is referred to in the following as the blood chamber, and a second chamber (4), through which dialysis fluid (e.g., a dialysate) flows and which is referred to in the following as the dialysis fluid chamber. The first chamber (3) is incorporated in an extracorporeal blood circuit (the right side of FIG. 1), while second chamber (4) is incorporated in dialysis fluid system of the HDF system (the left side of FIG. 1). The flow rate between the membranes (2) (e.g., the membrane flow rate) is shown by Qm.

The extracorporeal blood circuit includes an arterial blood line (6), which leads to inlet (3a) of blood chamber (3), and a venous blood line (7), which leads away from outlet (3b) of blood chamber (3) of dialyzer (1). The patient's blood is conveyed through blood chamber (3) of dialyzer (1) by an arterial blood pump (8) (e.g., a roller pump), which is disposed on arterial blood line (6). The blood pump (8) feeds blood to blood chamber (3) of the dialyzer at a specific blood flow rate Qb. Blood lines (6), (7) and dialyzer (1) may form a disposable intended for one-off use, which is inserted into the HDF system for the HDF treatment. In some variations, an air separator (e.g., drip chamber) may be incorporated into the arterial and venous blood line in order to eliminate air bubbles.

The fresh dialysis fluid is made available in a dialysis fluid source (9), which is described in further detail in FIG. 2. The dialysis fluid system may include the dialysis fluid source (9) along with other lines such as a dialysis fluid supply line (10) and a dialysis fluid discharge line (11). For instance, a dialysis fluid supply line (10) leads from dialysis fluid source (9) to an inlet (4a) of dialysis fluid chamber (4) of dialyzer (1). A dialysis fluid discharge line (11) leads from outlet (4b) of dialysis fluid chamber (4) to a drain (12). A first dialysis fluid pump (13) is incorporated in dialysis fluid supply line (10) and a second dialysis fluid pump (14) is incorporated in dialysis fluid discharge line (11). First dialysis fluid pump (13) conveys dialysis fluid from the dialysis fluid source at a specific dialysis fluid supply rate Qdi to inlet 4a of dialysis fluid chamber (4), while second dialysis fluid pump (14) conveys dialysis fluid at a specific dialysis fluid flow rate Qdo from outlet (4b) of dialysis fluid chamber (4) to drain (12).

During the HDF treatment, dialysis fluid may be fed from the dialysis fluid system as a substitution fluid to extracorporeal blood circuit via a substitution fluid line (15), which branches off from dialysis fluid supply line (10) upstream of first dialysis fluid pump (13). For instance, during the HDF treatment, a portion of the dialysis fluid may be separated (e.g., by a filter). The first portion of the dialysis fluid may become the substitution fluid that is provided to the substitution fluid line (15) and the second portion of the dialysis fluid may be provided to the dialyzer (1).

Substitution fluid line (15) comprises two line sections (15a) and (15b). One line section (15a) leads to arterial blood line (6) and the other line section (15b) leads to venous blood line (7).

The substitution fluid is conveyed using a pump (16) (e.g., a roller pump), into which substitution fluid line (15) is inserted. The substitution rate of the pump is Qs. A sterile filter (17) divided into two chambers (17a and 17b) is incorporated into substitution fluid line (15) upstream of the pump (16) (e.g., a substitution pump). The pump (16) together with the respective lines and the sterile filter form the substitution device of the HDF system. In order to pinch off the two line sections (15a and 15b) of substitution fluid line (15), shut-off elements, for example hose clamps or valves, may be provided, which however are not represented for the sake of better clarity. While only one sterile filter (17) is shown, the HDF system may include multiple filters (e.g., two filters). For instance, a first filter may be on the fluid supply line (10) prior to the split of the supply line (10) and the substitution fluid line (15). The second filter may be located in the same position as sterile filter (17). Additionally, and/or alternatively, the first filter may be on the fluid supply line (10) prior to the split and the second filter may be at the split of the supply line (10) and the substitution fluid line (15).

Blood pump (8), the first and second dialysis fluid pumps (13 and 14), and the pump (16) are connected via control lines (8', 13', 14', 16') to a controller (e.g., controller 402 shown in FIG. 4), from which the pumps are controlled taking account of the preset treatment parameters.

Blood pump (8) as well as first and second dialysis fluid pumps (13 and 14) are operated in order to operate the HDF system as a hemodialysis apparatus, dialysis fluid flowing through dialysis fluid chamber (4) of dialyzer (1). The pump (16) is operated in order to operate the HDF system as a hemodiafiltration apparatus, so that sterile dialysis fluid flows as a substitution fluid via sterile filter (17) optionally to arterial admission point (19) downstream of pump (8) and upstream of blood chamber (3) (pre-dilution) or to venous admission point (20) downstream of the blood chamber (post-dilution). Operation of the HDF system solely as a hemofiltration apparatus is however also possible (e.g., if first dialysis fluid pump (13) is not operated and therefore the inflow of dialysis fluid into the dialysis fluid chamber of the dialyzer is interrupted).

Furthermore, the HDF system provides NO within the substitution fluid either pre-dilution (e.g., via arterial admission point 19) or post-dilution (e.g., via venous admission point (20)). For instance, the dialysis fluid source (9) may provide NO so as to introduce NO into the blood stream of the patient during HDF treatment. As shown, the HDF system may provide the NO pre-dilution or post-dilution. By providing NO pre-dilution, the substitution would enter the blood side of the membrane itself. This may reduce coagulation in the membrane and enhance endothelial health. For instance, during a pre-dilution HDF treatment, NO spiked substitution fluid is introduced to the extracorporeal circuit prior to the dialyzer (1) and may provide anti-thrombogenic properties and reduce clotting on or in the dialyzer membrane (2). By providing NO post-dilution, the NO might not be exposed to the membrane. Further, during a post-dilution HDF treatment, introduction of substitution fluid into the blood can be after the blood has been concentrated from ultrafiltration (while passing through the dialyzer 1). In post-dilution treatment, the blood may be hemo-concentrated while passing through the dialyzer. NO spiked substitution fluid may be added to the blood after it passes through the dialyzer (1), reconstituting the blood and simultaneously administering a precise dose of NO to the patient. By using this treatment, the NO is designed to improve the endothelial and cardiovascular health of the patient. Additionally, and/or alternatively, the HDF system may provide NO directly to the blood chamber (3).

The measuring devices (21A-21C) may be used as measuring devices or sensors that are connected to a controller. For instance, the measuring device (21A) may be used for measuring the density of the blood, hematocrit (HCT) levels, pressure (e.g., venous pressure), and/or other measurements. Further, the measuring device (21A) may include a transmitter (21A') and a receiver (21A"). The measuring device (21C) may be used for measuring the density of the blood, HCT levels, pressure (e.g., arterial pressure) in the arterial line (6). The measuring device (21B) may be used to measure the density of the blood and/or other measurements upstream of the venous admission point (20) and downstream of the blood chamber (3). Additionally, and/or alternatively, the HDF system may include additional measuring devices that measure characteristics of the patient's blood during HCT treatment. For example, the HDF system may include a carbon monoxide (CO) oximeter to measure the concentration of methemoglobin, which increases in concentration in the blood stream as more NO is added. By measuring methemoglobin, the HDF system may measure the patient's NO levels in real-time by maintaining the methemoglobin below a certain threshold (e.g., a 5% threshold, which is safe for patients). Further, the real-time measurement may protect the patient from having too high of an NO dose during HDF treatment.

In some instances, a controller controls the pump (16) to control the delivery rate during HDF treatment. For instance, the controller may control the pump (16) to provide a certain amount of NO to the patient over a period of time (e.g., a rate of NO provided to the patient). The controller may further control providing the NO either pre-dilution or post-dilution. The operation of the controller will be described in further detail below.

The blood treatment apparatus of FIG. 1 is merely exemplary and the HDF system that uses NO may include additional and/or alternative embodiments (e.g., additional and/or alternative components) of a blood treatment apparatus (e.g., a blood circuit) for providing NO during HDF treatment for a patient. For example, the blood treatment apparatus can be, e.g., the blood treatment apparatus in Noack et al., U.S. Pat. No. 8,216,478, the hemodiafiltration delivery module in Collins et al., U.S. Pat. No. 10,821,216, and/or the extracorporeal circulation and the dialysis fluid circulation with a hemodialyzer and a hemofilter Tschulena et al., U.S. Pat. No. 10,172,994, which are hereby incorporated herein in their entirety.

FIG. 2 shows a block diagram illustrating an exemplary mixing system according to one or more examples of the disclosure. For instance, the mixing system (200) includes a water source (202), a chemical dispenser (206), a nitric oxide dispenser (208), and a mixing chamber (204). The water source (202) provides water to the mixing chamber (204).

The chemical dispenser (206) may include chemical sources that provide chemical concentrates. The chemical concentrates are used as ingredients of the dialysis fluid (e.g., the dialysate mixture and the substitution fluid mixture). The chemical concentrates may be liquid concentrates of varying viscosity or may be solid concentrates in the form of tablets, pills, or powders. The chemical sources are containers that hold these chemical concentrates. The chemical dispenser (206) may thus hold concentrates of potassium chloride (KCl), calcium chloride ($CaCl_2$), magnesium chloride ($MgCl_2$), citric acid, dextrose, sodium chloride (NaCl), sodium bicarbonate (NaHCO3), acetic acid, glucose, and so on. Not all chemical concentrates available need to be used for every dialysate formula or recipe or substitution fluid formula or recipe.

The chemical dispenser (206) may further include actuators that aid in dispensing specific amounts of the chemical concentrates to the mixing chamber (204) for mixing a batch of the dialysis fluid (e.g., the dialysate for the dialyzer (1) and/or substitution fluid for pre-dilution and/or post-dilution). The actuators may control the amount of chemical concentrates provided to the mixing chamber (204), and may also control an amount of water used in mixing the batch of dialysis fluid from the water source (202). A water source (202) may be a water connection for receiving filtered water or water suitable for use in dialysis treatment.

The chemical dispenser (206) and/or the water source (202) provide the chemical concentrates and water to the mixing chamber (204). Contents in the mixing chamber (204) are agitated for an appropriate amount of time until chemical concentrates are sufficiently distributed throughout. In some instances, the mixing chamber (204) increases its temperature to assist in dissolving and/or distributing the chemical concentrates to yield a homogenous solution. After realizing a homogenous solution, the mixing chamber (204) may be brought to an appropriate temperature for HDF treatment.

The mixing chamber (204) of the mixing system (200) provides the mixed dialysis fluid to a dialyzer such as the dialyzer (1) shown in FIG. 1 and/or to a sterile filter such as a sterile filter (17) shown in FIG. 1, which then provides it onwards to the admission points for pre-dilution or post-dilution (e.g., arterial admission point (19) and/or venous admission point (20)). In some examples, the mixing chamber (204) is multi-chambered where a first chamber is used for mixing the dialysis fluid and a second chamber is used for storing and delivering the dialysis fluid.

In some variations, the mixing chamber (204) may include sensors for sensing levels of the dialysis fluid in the first and/or second chambers. The mixing chamber (204) may further include components (e.g., sensors) for alerting a controller when a batch of dialysis fluid has been mixed and when they are provided onwards.

The mixing system (200) further includes an NO dispenser (208) that provides NO to the mixing chamber (204). For example, the NO dispenser (208) may include an NO source that provides NO. In some instances, the NO dispenser (208) may use NO in a liquid state (e.g., S-nitrosoglutathione and S-nitrosocysteine) that is provided to the mixing chamber (204). For instance, the NO dispenser (208) may include the NO source and one or more actuators that are configured to provide NO to the mixing chamber (204).

Additionally, and/or alternatively, the NO dispenser (208) may use an NO source that provides NO in a gaseous form. For instance, the NO dispenser (208) includes an NO gas supply source that provides NO, a flow meter connected to the NO gas supply source, and an NO gas supply path with pressure gauges and medical gas filters to ensure the sterility of the gas. The NO dispenser (208) may further include a component to dissolve the NO gas into a liquid prior to providing it to the mixing chamber (204).

In some examples, the NO dispenser (208) may provide the NO to the water source (202). For example, instead of the NO dispenser (208) providing the NO to the mixing chamber (204), the NO dispenser (208) may provide the NO to the water source (202), which provides a more pure NO as it may pass more filters. As such, this example may provide another step to purify the NO before it reaches the dialyzer or the patient.

The mixing system (200) is merely exemplary and the HDF system that uses NO may include additional and/or alternative embodiments (e.g., additional and/or alternative components) of a mixing system for providing NO during HDF treatment for a patient.

Figure 3A:
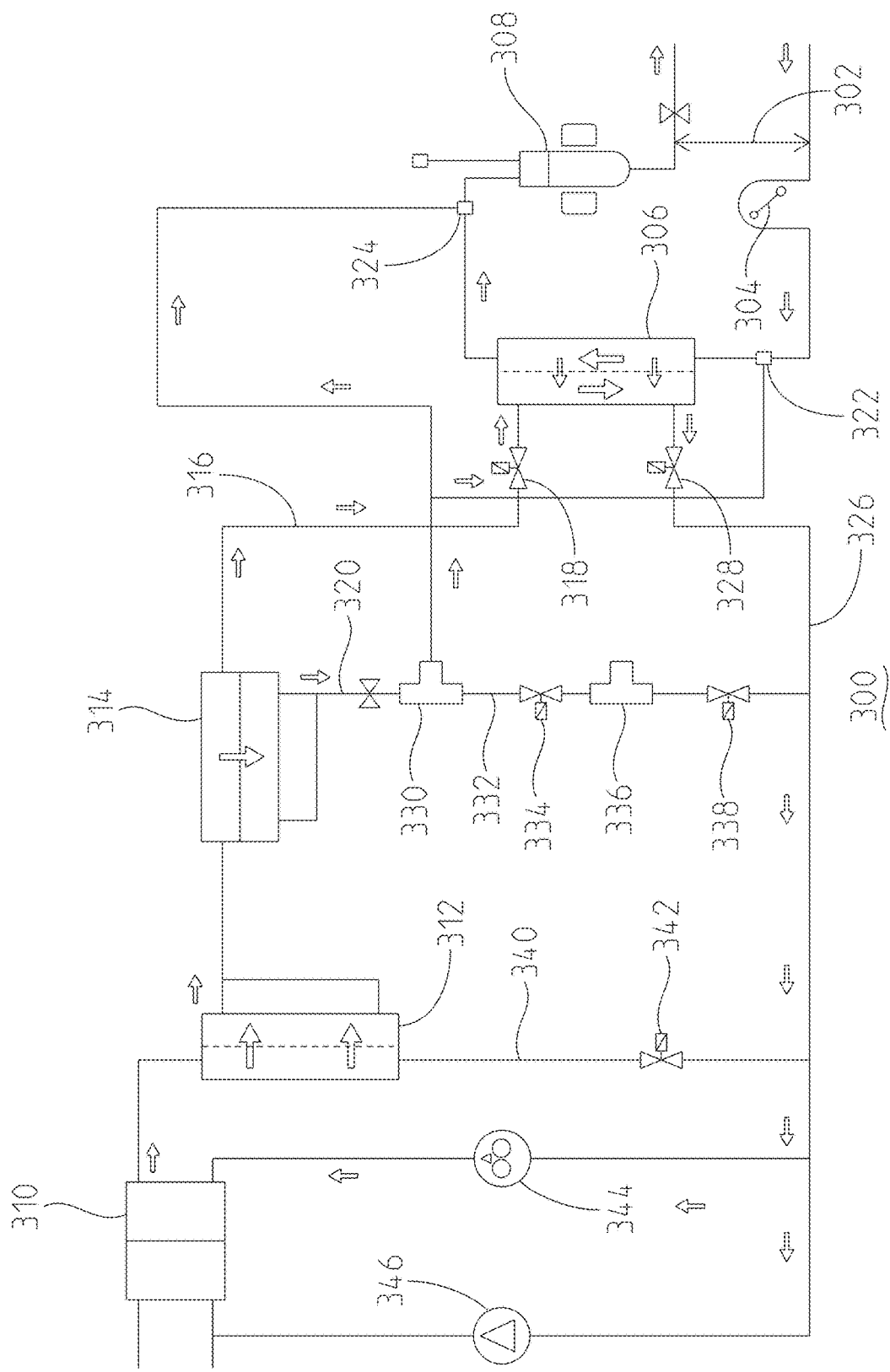
FIG. 3A shows another exemplary extracorporeal blood treatment apparatus for a hemodiafiltration system according to one or more examples of the disclosure.

FIG. 3A shows another exemplary extracorporeal blood treatment apparatus for a hemodiafiltration system according to one or more examples of the disclosure. For example, the extracorporeal blood treatment apparatus (300) may include similar and/or additional components to the extracorporeal blood treatment apparatus of FIG. 1. For instance, as shown, blood lines (302) are included that are similar to the arterial blood line (6) and the venous blood line 7 of FIG. 1. A pump (304) is used to convey blood through the blood lines (302). For instance, the pump (304) may be an arterial blood pump such as the arterial blood pump (8) shown in FIG. 1. The pump (304) moves the patient's blood through the dialyzer (306), which may be similar to the dialyzer 1 of FIG. 1 and may include two blood chambers as well as a semi-permeable membrane. The dialysis fluid may be provided to one of the two blood chambers of the dialyzer (306). The arrows within the dialyzer (306) show the direction of the blood flow in one of the chambers, the direction of the dialysis fluid flow in the other chamber, and transport of the substances of the blood through the semi-permeable membrane. Afterwards, in the blood line (302) is a venous drip chamber (308) (e.g., a venous bubble catcher, which may include one or more air detectors). The venous drip chamber (308) is a protective system provides the blood back to the patient.

A dialysis fluid balancing chamber (310) that provides precise volumetric control of the dialysis fluid and substitution circuit flows is also included. The filters (312 and 314) are sterile filters that may be similar to the filter (17) shown in FIG. 1. The filters (312 and 314) (e.g., DIASAFE filters) may include two chambers for filtering the dialysis fluid. In some instances, the filters (312 and 314) may be other types of filters (e.g., types of filters other than DIASAFE filters). The first filter (312) provides a first filtering of the dialysis fluid. The second filter (314) also provides filtering as well as separates the dialysis fluid. For instance, the second filter (314) is connected to a dialysate line (316) that provides a first portion of the dialysis fluid to the dialyzer (306). A valve (318) is provided in the dialysate line (316). The second filter (314) is also connected to a substitution fluid line (320) that provides a second portion of the dialysis fluid (e.g., the substitution fluid) for HDF treatment. The substitution fluid line (320) connects to the blood line (302) at admission points (322 and 324). For instance, the admission point (322) may be an arterial admission point such as the arterial admission point (19) of FIG. 1, which is upstream of the dialyzer (306) for pre-dilution. The admission point (324) may be a venous admission point such as the venous admission point (20) of FIG. 1, which is downstream of the dialyzer (306) for post-dilution. The NO may be provided to either of the admission points (322 and 324) for pre-dilution or post-dilution.

In some instances, the first filter (312) acts as a dead-end filter, with all liquid being forced across the membrane. In some examples, the second filter (314) is a tangential filter, where pressures are used to pull liquid across the membrane from the main flow of liquid that is otherwise passing straight through the lines (e.g., remaining unfiltered by the second filter (314)). As such, the retentate (e.g., the dialysate or the first portion of the dialysis fluid) moves through the dialysate line (316). In contrast, the permeate (e.g., the substitution fluid or the second portion of the dialysis fluid)

is pulled from the dialysate circuit that is passing through the second filter (314) and is being simultaneously filtered a second time as it is pulled across the membrane of the second filter (314). The permeate from the second filter (314) meets the requirement for substitution fluid per International Organization for Standardization (ISO) 23500 and ISO 11663. This permeate then proceeds to the substitution fluid line (320). Therefore, the distinction between the dialysate and substitution fluid may include the unique sterility and pyrogenicity requirements for a liquid indicated for infusion.

The dialyzer (306) is also connected to a discharge line (326), which may be similar to the fluid discharge line (11) of FIG. 1. Thus, this discharge line (326) may be to a drain. The valve (328) is included in the discharge line (326). Furthermore, the component (330) may be a connector (e.g., a replacement-fluid port) that splits the substitution fluid line (320). For instance, the connector (330) may connect the substitution fluid line (320) to a substitution fluid drainage line (332). The substitution fluid drainage line (332) may include a connector (336) (e.g., a rinse/filtrate port) and two valves (334 and 338). Another drainage line (340) is connected to the first filter (312) that allows drainage from the first filter (312). The drainage line (340) includes a valve (342) (e.g., a retentate valve).

Additionally, there are two pumps (344 and 346). The first pump (344) is a flow pump and the second pump (346) is an ultrafiltration pump. The pump (344) in the effluent dialysate circuit drives the flow of dialysate from the dialyzer (306 and the pump 346) generates additional pressure within the dialysate chamber of the dialyzer (306) sufficient to force convective transport of liquid and solute from the blood, across the membrane, and into the dialysate circuit.

In some examples, one or more additional filters may be used to filter the dialysis fluid. For instance, another filter may be included in the substitution fluid line (320) to further filter the substitution fluid prior to providing it to the patient.

The extracorporeal blood treatment apparatus (300), including the rates, shown in FIG. 3A is merely exemplary and can include additional/alternative components and/or rates.

Figure 3B:
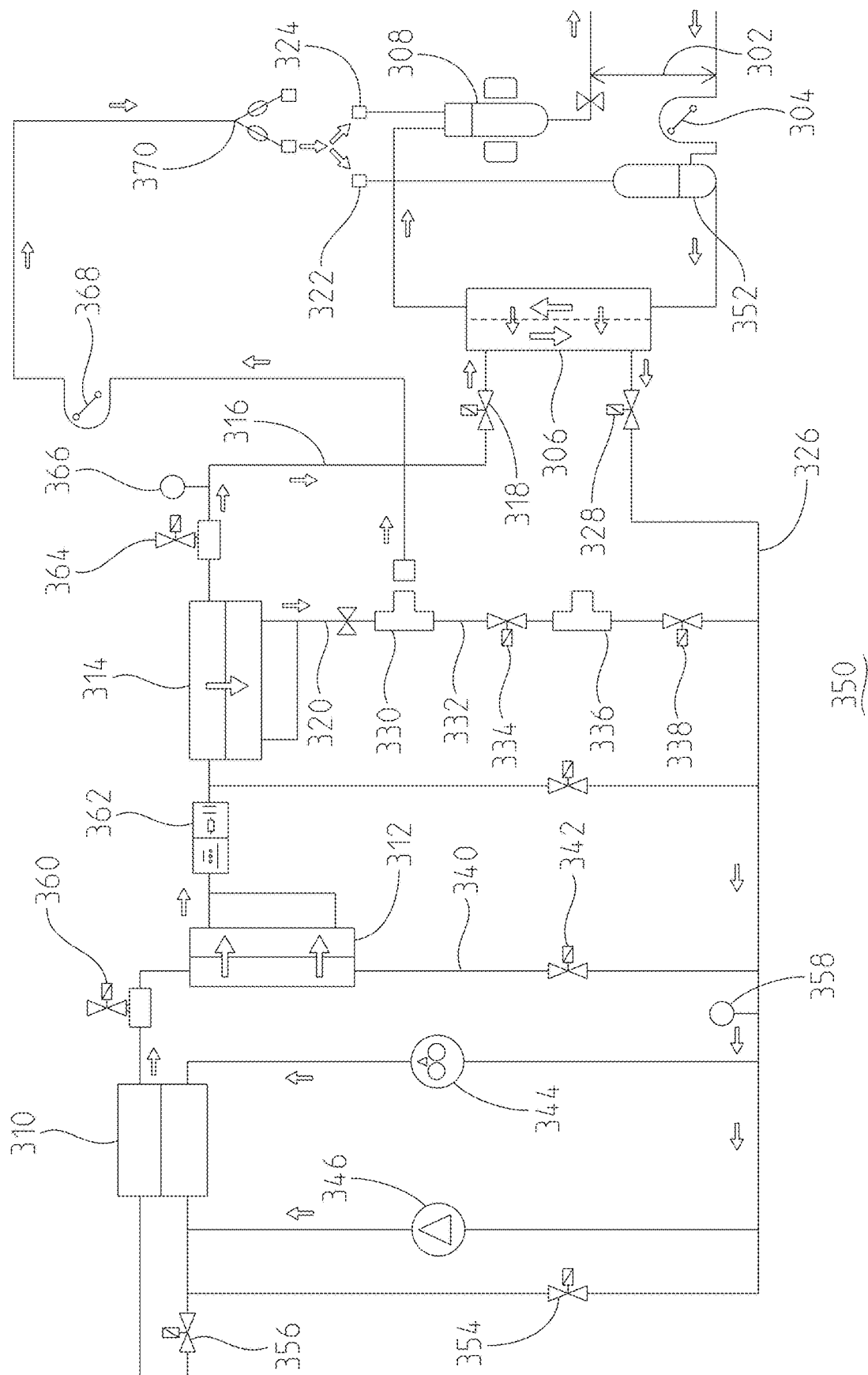
FIG. 3B shows yet another exemplary extracorporeal blood treatment apparatus for a hemodiafiltration system according to one or more examples of the disclosure.

FIG. 3B shows yet another exemplary extracorporeal blood treatment apparatus for a hemodiafiltration system according to one or more examples of the disclosure. For example, the extracorporeal blood treatment apparatus (350) may include similar and/or additional components to the extracorporeal blood treatment apparatus of FIG. 3A. Further, the extracorporeal blood treatment apparatus (350) may include further components and/or devices. For instance, the apparatus (350) includes an arterial bubble catcher (352) that may function similarly to the venous bubble catcher (308), but on the arterial blood line. Additionally, two additional valves (354 and 356) are shown. Valve (354) is a fill valve and valve (356) is a drain valve.

The apparatus (350) further includes a vent valve and hydrophobic filter (360), a pressure transducer (358), a condition and temperature monitoring device (362), a filter/test valve (364), and a pressure transducer (366). The pressure transducers (358 and 366) detect and provide pressure measurements to a controller (e.g., controller 402). The vent valve and hydrophobic filter (360) may be employed during calibration of pressure transducers (e.g. sensor 366). The sensor cluster (362) monitors the conductivity and temperature of the effluent flow from filter (312). The filter/test valve (364) is utilized during internal pressure tests.

In addition, in the substitution line (320), a pump (368) is included. The pump (368) may be similar to the pump (16) of FIG. 1. Additionally, a Y-connector (370) is also included in the substitution line (320) that separates the substitution fluid for pre-dilution and post-dilution via the administration points (322 and 324).

Figure 4:
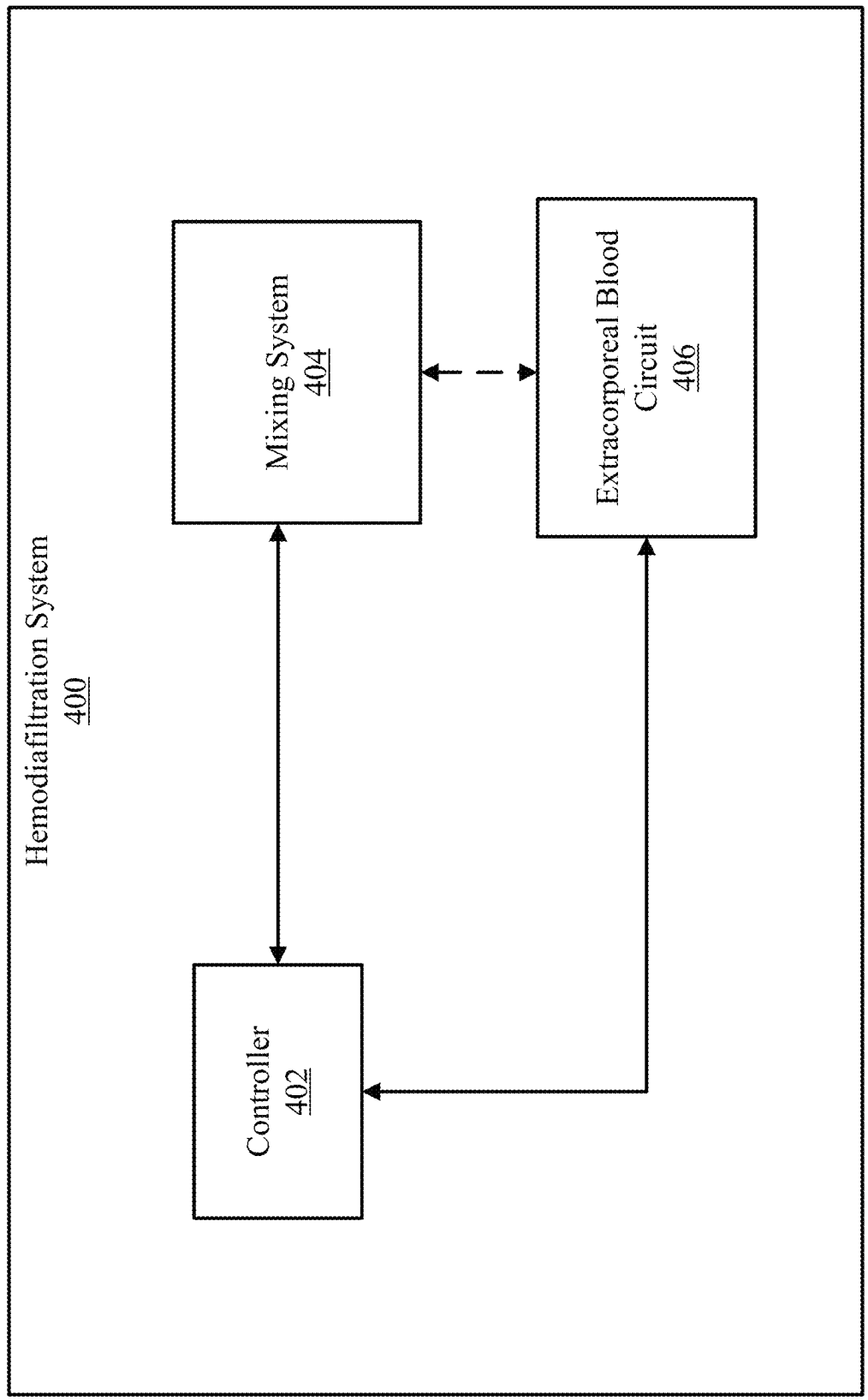
FIG. 4 shows a block diagram illustrating an exemplary hemodiafiltration system according to one or more examples of the disclosure.

FIG. 4 shows a block diagram illustrating an exemplary hemodiafiltration system according to one or more examples of the disclosure. For instance, the hemodiafiltration (HDF) system (400) includes one or more controllers (402), a mixing system (404), and an extracorporeal blood circuit (406). The mixing system (404) may be the mixing system (200) shown in FIG. 2. The extracorporeal blood circuit (406) may be and/or include the components shown in FIGS. 1 and 3, and is used to perform the HDF treatment. The dotted line shows the connection between the mixing system (400) and the extracorporeal blood circuit (406), which may include the dialysis fluid that flows to the extracorporeal blood circuit (406).

The controller (402) may be any type of hardware and/or software logic, such as a central processing unit (CPU), a field programmable gate array (FPGA), an application specific integrated circuit (ASIC), a processor with non-transitory computer-readable medium, a RASPBERRY PI processor/logic, and/or logic, that executes computer executable instructions for performing the functions, processes, and/or methods described herein. For example, the controller (402) may control the components of the mixing system (404) (e.g., actuators) and/or the components of the extracorporeal blood circuit (406) (e.g., the pumps, valves, sensors, and/or other components described in FIGS. 1 and 3). For instance, the controller (402) may provide instructions to mix the dialysis fluid, which includes providing NO from the NO dispenser (208). Further, the controller (402) may provide instructions to release the mixed dialysis fluid to the extracorporeal blood circuit (406). In addition, the controller (402) may provide instructions to the pumps, valves, and so on to perform the HDF treatment for the patient. In some instances, the controller (402) may obtain user input from a monitor or user device. The user input may indicate a flow rate for controlling the HDF treatment, including the amount of NO to provide during the HDF treatment. For example, based on the user input, the controller (402) may indicate the amount and/or rate of NO that is provided for mixing in the mixing chamber and/or provided during the HDF treatment. For instance, the controller (402) may control the pump (16 of FIG. 1), to control the rate that the substitution fluid is provided to the patient. In some instances, the controller (402) may control the amount of NO provided to the patient based on individual characteristics of the patient (e.g., based upon a recipe associated with the patient). For example, the controller (402) may control the amount of NO provided by the NO dispenser (208) and/or the pump rate of the substitution fluid based on an individualized recipe for the patient.

Figure 5:
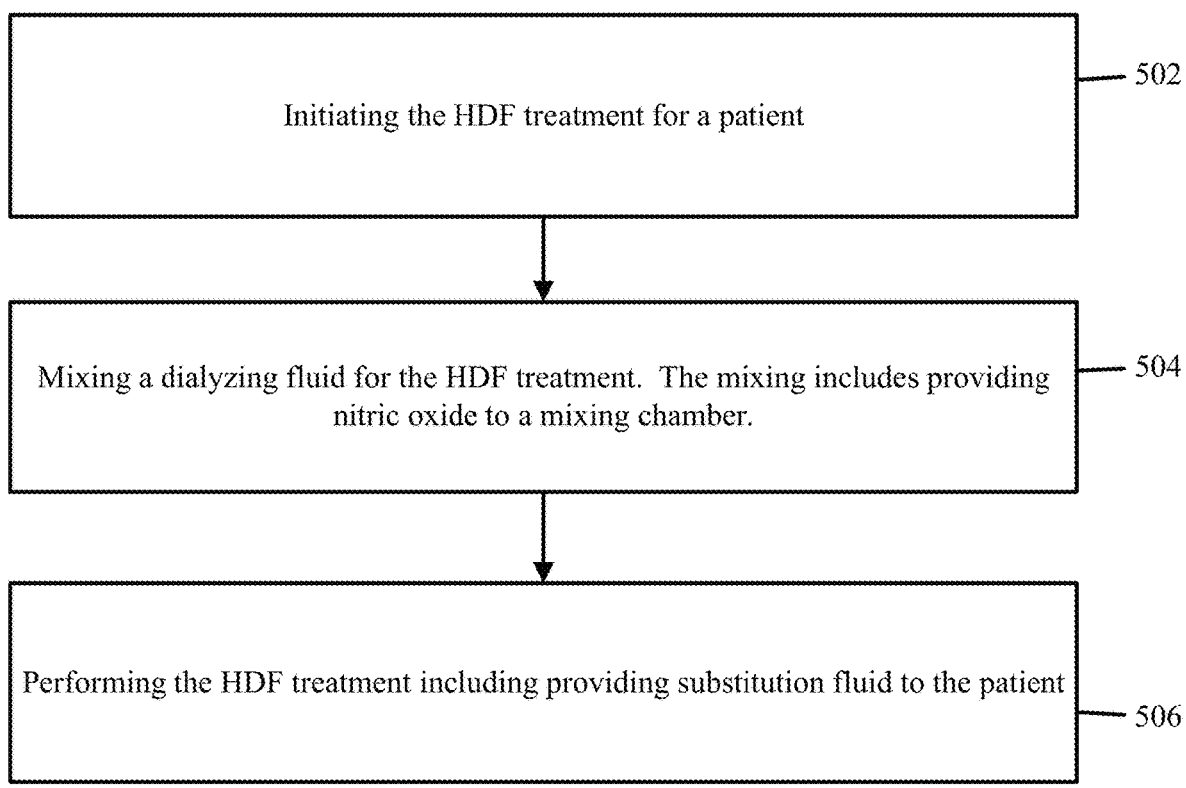
FIG. 5 shows a flowchart of an exemplary process for using the hemodiafiltration system according to one or more examples of the disclosure.

FIG. 5 shows a flowchart of an exemplary process for using the hemodiafiltration system according to one or more examples of the disclosure. FIG. 5 shows a flowchart illustrating a process (500) that a controller (e.g., controller (402)) may use to perform the HDF treatment.

At block (502), the controller 402 initiates the HDF treatment for a patient. For example, the controller (402) may receive user input indicating to start the HDF treatment.

At block (504), the controller (402) mixes a dialysis fluid for the HDF treatment. The mixing includes providing nitric oxide to a mixing chamber of the HDF system. For instance, the controller (402) controls the chemical dispenser (206) and/or the NO dispenser (208) (e.g., the actuators of the dispensers) to dispense an amount of chemical to provide to the mixing chamber (204). In some instances, the controller (402) may control the amount of the NO that is provided by the NO dispenser (208). Subsequently, the controller (402) may control a valve to provide the dialysis fluid to the extracorporeal blood circuit (406).

At block (506), the controller (402) performs the HDF treatment including providing the substitution fluid to the patient. For instance, the controller (402) may use the filters (314 and/or 17) from FIG. 1 or 3 to separate the dialysis fluid into a first portion (e.g., a dialysate that is provided to the dialyzer) and a second portion (e.g., the substitution fluid), and provide the substitution fluid to the patient at the admission points for pre-dilution and/or post-dilution.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A hemodiafiltration (HDF) system for performing HDF treatment, comprising:
    a mixing system, comprising:
        a nitric oxide dispenser configured to provide nitric oxide (NO) to a mixing chamber;
        a chemical dispenser configured to provide chemicals to the mixing chamber; and
        the mixing chamber configured to mix the NO and the chemicals to produce a dialysis fluid;
    an extracorporeal blood circuit, comprising:
        a filter configured to separate the dialysis fluid into a dialysate and NO spiked substitution fluid;
        a dialyzer configured to receive the dialysate from the filter; and
        a blood line connected to the dialyzer and comprising one or more admission points, wherein the one or more admission points are connected to the filter and the NO spiked substitution fluid is administered during the HDF treatment using the one or more admission points; and
    a controller configured to:
        provide instructions to the mixing system to produce the dialysis fluid comprising the NO; and
        provide instructions to the extracorporeal blood circuit to perform the HDF treatment using the dialysate and the NO spiked substitution fluid.

2. The HDF system of claim 1, wherein the blood line comprises an arterial blood line and a venous blood line, wherein the arterial blood line feeds blood from the patient to a blood chamber of the dialyzer, wherein the venous blood line provides the blood of the patient from the blood chamber back to the patient, and
    wherein the one or more admission points is an arterial admission point that is on the arterial blood line and configured to provide the NO spiked substitution fluid prior to the blood chamber for pre-dilution HDF treatment.

3. The HDF system of claim 1, wherein the blood line comprises an arterial blood line and a venous blood line, wherein the arterial blood line feeds blood from the patient to a blood chamber of the dialyzer, wherein the venous blood line provides the blood of the patient from the blood chamber back to the patient, and
    wherein the one or more admission points is a venous admission point that is on the venous blood line and configured to provide the NO spiked substitution fluid after the blood chamber for post-dilution HDF treatment.

4. The HDF system of claim 1, wherein the filter comprises a membrane, a first chamber, and a second chamber, and wherein the filter is configured to separate the dialysis fluid by having a first portion of the dialysis fluid not pass through the membrane and remain in the first chamber and a second portion of the dialysis fluid pass through the membrane to enter the second chamber, wherein the first portion of the dialysis fluid is the dialysate and the second portion of the dialysis fluid is the NO spiked substitution fluid.

5. The HDF system of claim 4, wherein the extracorporeal blood circuit further comprises:
   a dialysate line that connects the first chamber of the filter to the dialyzer; and
   a substitution fluid line that connects the second chamber of the filter to the one or more admission points.

6. The HDF system of claim 1, wherein the nitric oxide dispenser comprises a nitric oxide source, and wherein the nitric oxide source provides nitric oxide in a liquid form.

7. The HDF system of claim 1, wherein the nitric oxide dispenser comprises a nitric oxide source, and wherein the nitric oxide source provides nitric oxide in a gaseous form.

8. The HDF system of claim 1, wherein providing the instructions to the mixing system to produce the dialysis fluid comprises:
   providing instructions to the nitric oxide dispenser to dispense a set amount of NO to the mixing chamber.

9. The HDF system of claim 1, wherein the extracorporeal blood circuit further comprises:
   a pump configured to pump the NO spiked substitution fluid into the one or more admission points, and wherein providing the instructions to the extracorporeal blood circuit to perform the HDF treatment comprises controlling a rate that the pump supplies the NO spiked substitution fluid into the one or more admission points.

10. A hemodiafiltration (HDF) system for performing HDF treatment, comprising:
    a controller configured to:
      provide instructions to produce dialysis fluid comprising nitric oxide (NO); and
      provide instructions to perform the HDF treatment using the dialysis fluid comprising the NO; and
    an extracorporeal blood circuit, comprising:
      a filter configured to separate the dialysis fluid into a dialysate and NO spiked substitution fluid;
      a dialyzer configured to receive the dialysate from the filter; and
      a blood line connected to the dialyzer and comprising one or more admission points for administering the NO spiked substitution fluid during the HDF treatment.

11. The HDF system of claim 10, wherein the blood line comprises an arterial blood line and a venous blood line, and
    wherein the one or more admission points is an arterial admission point that is on the arterial blood line and configured to administer the NO spiked substitution fluid prior to the dialyzer for pre-dilution HDF treatment.

12. The HDF system of claim 10, wherein the blood line comprises an arterial blood line and a venous blood line, and
    wherein the one or more admission points is a venous admission point that is on the venous blood line and configured to administer the NO spiked substitution fluid after the dialyzer for post-dilution HDF treatment.

13. The HDF system of claim 10, wherein the filter comprises a membrane, a first chamber, and a second chamber, and wherein the filter is configured to separate the dialysis fluid by having a first portion of the dialysis fluid not pass through the membrane and remain in the first chamber and a second portion of the dialysis fluid pass through the membrane to enter the second chamber, wherein the first portion of the dialysis fluid is the dialysate and the second portion of the dialysis fluid is the NO spiked substitution fluid.

14. The HDF system of claim 13, wherein the extracorporeal blood circuit further comprises:
    a dialysate line that connects the first chamber of the filter to the dialyzer; and
    a substitution fluid line that connects the second chamber of the filter to the one or more admission points.

15. The HDF system of claim 10, wherein providing the instructions to produce the dialysis fluid comprising NO comprises:
    providing instructions to a nitric oxide dispenser to dispense a set amount of NO to a mixing chamber.

* * * * *